United States Patent [19]

Ross

[11] Patent Number: 5,237,881
[45] Date of Patent: Aug. 24, 1993

[54] INERTIAL DILUTION FILTER PROBE

[75] Inventor: Thaddeus C. Ross, Santa Barbara, Calif.

[73] Assignee: Anarad, Inc., Santa Barbara, Calif.

[21] Appl. No.: 840,960

[22] Filed: Feb. 21, 1992

[51] Int. Cl.⁵ ............................................. G01N 1/24
[52] U.S. Cl. .................................... 73/863.12; 55/270; 55/410; 73/863.23; 73/863.81; 73/864.81
[58] Field of Search .................. 55/270, 410, 468, 267, 55/DIG. 14; 73/863.11, 863.12, 863.23, 863.81, 864.81

[56] References Cited

U.S. PATENT DOCUMENTS

| | | | |
|---|---|---|---|
| 3,289,481 | 12/1966 | Barnes | 55/431 |
| 3,593,023 | 7/1971 | Dodson | 73/863.12 |
| 4,738,147 | 4/1988 | Tomlin | 55/270 |
| 4,817,441 | 4/1989 | Porowski et al. | 55/270 |
| 4,974,455 | 12/1990 | McGowan et al. | 73/863.12 |

*Primary Examiner*—Jay H. Woo
*Assistant Examiner*—James P. Mackey
*Attorney, Agent, or Firm*—Sachs & Sachs

[57] ABSTRACT

A filter probe for sampling components of a stack gas which includes means for extracting a flow sample of the stack gas, means for inertial filtering of the flowing stack gas sample extracted by the extracting means, means for collecting the flowing stack gas sample after filtering by the filtering means, means for conditioning the filtered and collected stack gas sample based on predetermined criteria such as cooling and drying, and means for flowing the filtered and collected stack gas sample from the collecting means to the extracting means so that a constant flow of the filtered stack gas sample is presented to the conditioning means to permit essentially instantaneous analysis of the stack gas sample.

24 Claims, 3 Drawing Sheets

INERTIAL DILUTION FILTER PROBE

BACKGROUND AND/OR ENVIRONMENT OF THE INVENTION

1. Field of the Invention

The present invention relates to apparatuses for analyzing a stack gas produced by combustion, and more particularly to a filter probe for sampling components of a stack gas which employs a non-clogging flow through inertial filter and means for conditioning the stack gas sample to optimize the analyzation thereof.

2. Description of the Contemporary and/or Prior Art

The desire to analyze stack gases produced by combustion processes is well known in the art. Typically, a sample extracted from the combustion process is drawn off by a sampling probe which is installed in a stack. The output of the probe then connects to sample line leading to remotely located analyzers. Depending upon how the probe is designed and how analysis takes place, the gases may need to be filtered, cooled, and dried in sample conditioning stages before being presented to the analyzers. Two of the currently employed major probe design styles differ as to whether the sample is sent down the line in an as is condition, that is hot, wet and at a full concentration or whether the sample is diluted with a neutral carrier gas, usually clean instrument air. Further, extraction probes usually include some kind of filtering medium so as to avoid loading the sample line with dust. One such probe includes a "inertial" bypass filter element which consists of a ceramic or metallic porous wall tube through which the gas extracted from the stack is drawn at a high speed. This element is attached to the outlet end of the probe which in itself is just a piece of straight pipe and is followed by an air driven eductor or jet pump to provide the suction for moving the gases through the probe and inertial filter, without the danger of clogging the straight inline bore of this device. A small portion of the total gas flow through the filter element permeates through the filter walls and is collected in a surrounding jacket from which it is drawn by a sample line to subsequent stages for analysis.

Particles entrained in the high velocity axial gas flow are precluded from deposition on the porous filter walls or from penetrating therethrough by the ballistic effect of particle inertia, hence the name "inertial" bypass filter. The low radially velocity of such devices also inhibits particles from penetrating the porous wall. Such devices are manufactured by Mott Metallurgical Corporation, Farmington Industrial Park, Farmington, Conn. and are disclosed in their brochure entitled Inertial Gas Sampling Filter Systems DB 4600.

A disadvantage of currently known diluting stack samplers is that an average of the analyzed components is presented rather than an instantaneous reading.

Another type of extraction probe employs a filter in the tip of the probe followed down stream by a dilution mixer made up of a critical flow orifice and eductor. The critical flow orifice limits the stack gas flow and is sized in conjunction with the air driven eductor in such a manner that the flow ratio between the orifice flow and the eductor air set up a defined dilution ratio.

This ratio is usually picked in the range of between 15 to 1 and 300 to 1 depending on the type of analyzer served. As a result, the hot stack gas is immediately diluted and therefore the sample has a reduction in temperature and moisture content which eliminates the need for additional sample conditioning before the gas is fed to the analyzers. An unfortunate disadvantage of this configuration is that the tip filter in the probe frequently clogs leading to frequent probe maintenance and the instability of the dilution ratio that depends on the uncertain relationship between the critical orifice and the eductor flows as a function of variations in the absolute stack pressure. Such a diluting stack sampler for monitoring gaseous emissions is manufactured by Environmental & Process Monitoring of Prospect, Illinois and is described in the Manual for Model 797 Diluting Stack Sampler.

SUMMARY OF THE INVENTION

Therefore, the primary object of the subject invention is to provide a filter probe for sampling components of a stack gas which dilutes the stack gas for optimal analysis.

A further object of the present invention is to provide a filter probe for sampling components of a stack gas wherein the filter material thereof does not clog as a result of exposure to the stack gas.

A still further object of the subject invention is to provide filter probe for sampling components of a stack gas which is essentially maintenance free, although exposed to wet and dirty stack sample.

Still another object of the present invention is provide a filter probe for sampling components of a stack gas which is rugged and trouble free.

Still another further object of the subject invention is to provide a filter probe for sampling components of a stack gas which permits instantaneous or real-time measurements to be made.

These objects as well as further objects and advantages of the present invention, will become readily apparent after reading the ensuing description of a non-limiting illustrative embodiment and viewing the accompanying drawings.

A filter probe for sampling components of a stack gas, according to the principles of the present invention, includes means for extracting a flowing sample of stack gas, extracting means having a flow input and a flow output; means for filtering the flowing stack gas sample extracted by the extracting means; means for collecting the flowing stack gas sample after filtering by the filtering means; means for conditioning the filtered and collected stack gas sample based on predetermined criteria, the conditioning means being in communication with the collecting means; and means for flowing the filtered and collected stack gas sample from the collecting means to the flow output of the extracting means so as to create a constant flow of the filtered stack gas sample to the conditioning means.

BRIEF DESCRIPTION OF THE DRAWINGS

In order that the present invention may be more fully understood, it will now be described, by way of example, with reference to the accompanying drawings in which.

DESCRIPTION OF THE PREFERRED EMBODIMENT

Figure 1:
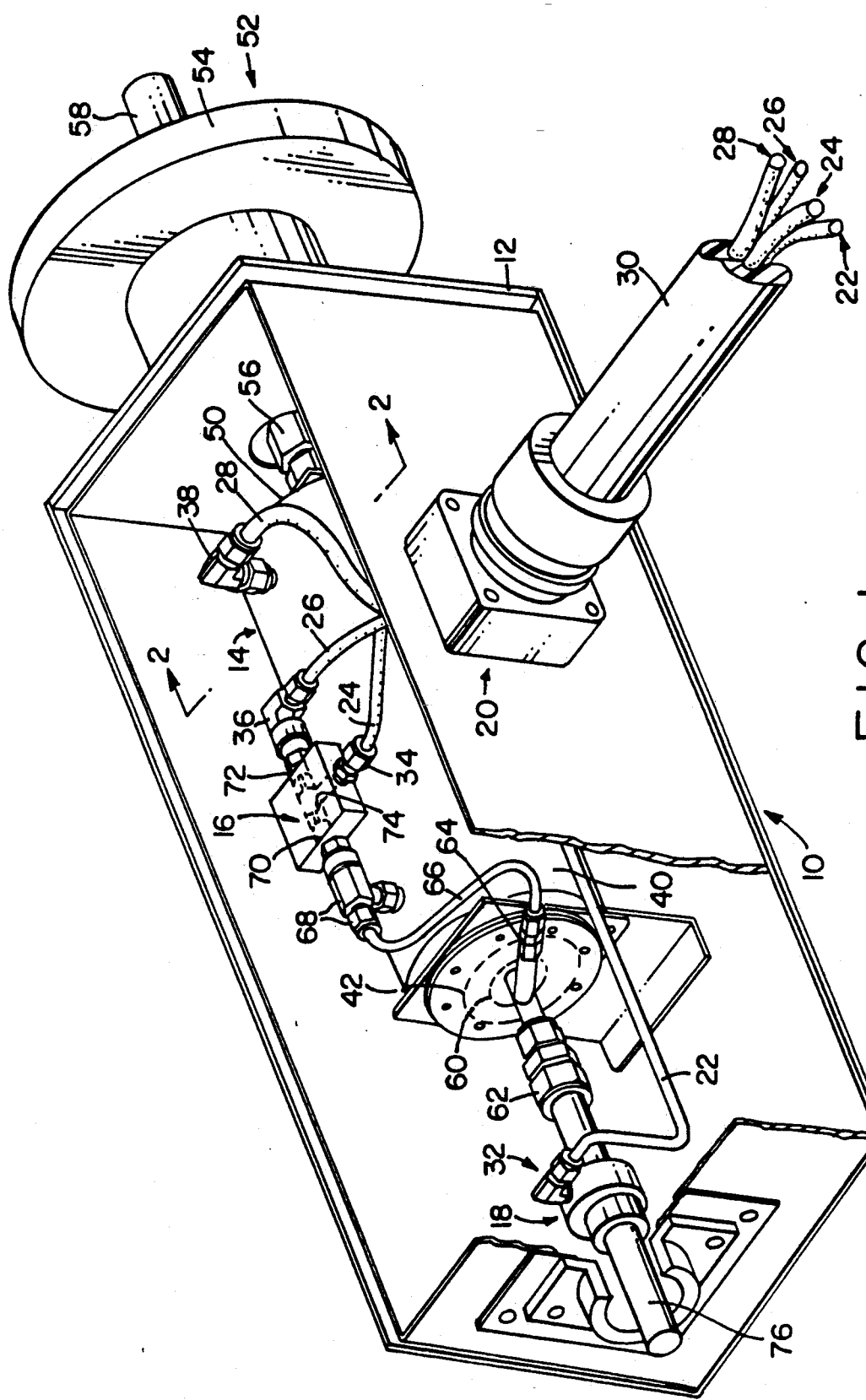
FIG. 1 is a partially broken away perspective view of a filter probe incorporating the principles of the present invention.
Figure 2:
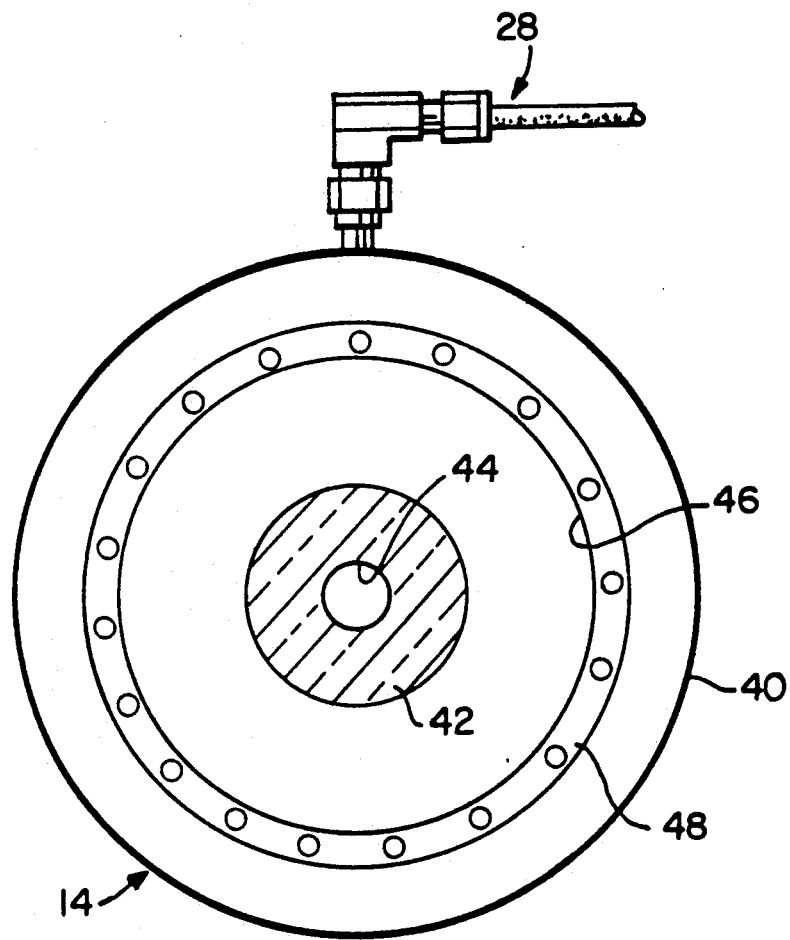
FIG. 2 is a cross sectional view taken substantially through the lines of 2—2 of FIG. 1.
Figure 3:
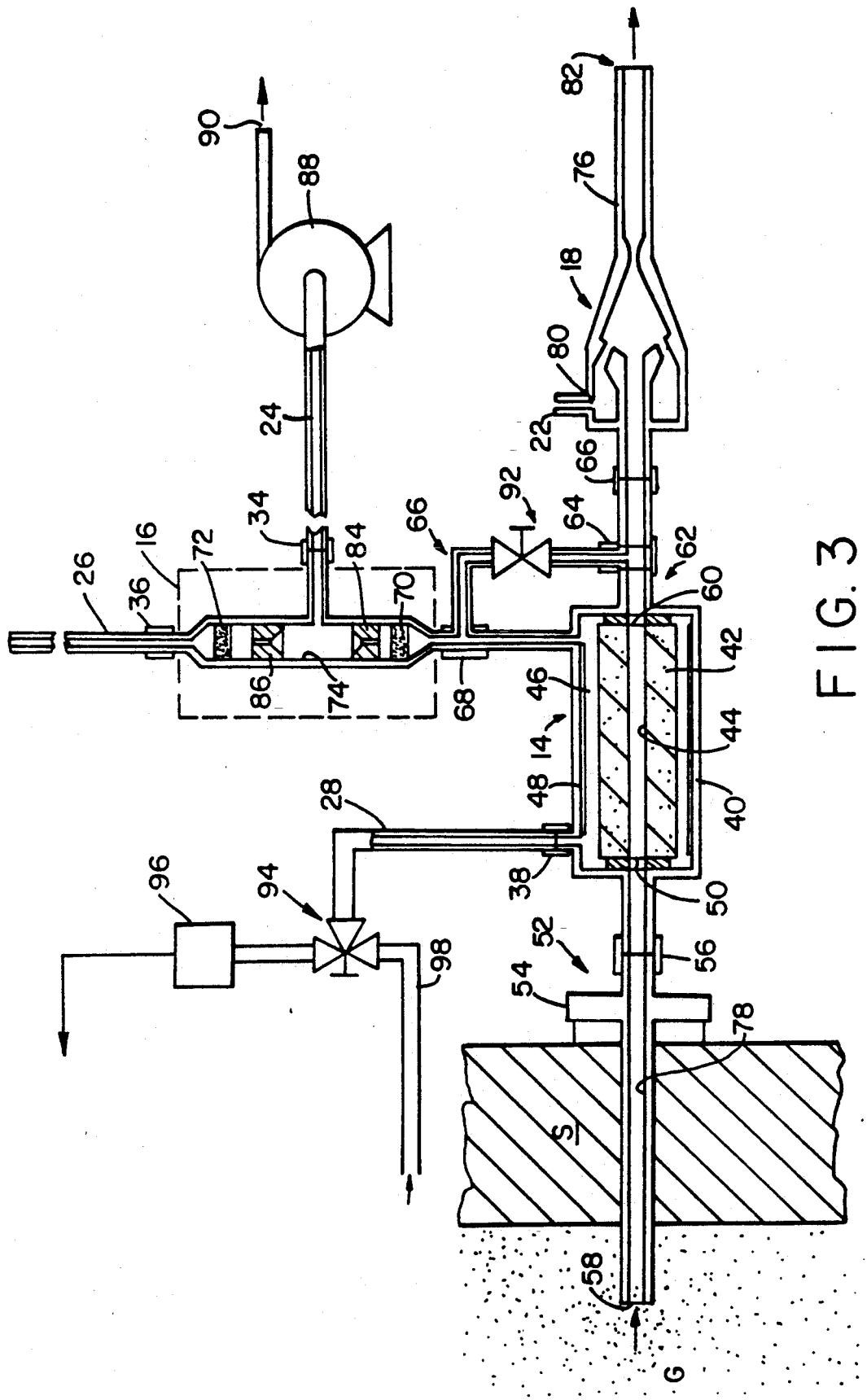
FIG. 3 is a pictorial representation of the preferred embodiment of the present invention.

Referring now to the figures and more particularly to FIGS. 1, 2 and 3 thereof, there is illustrated therein a filter probe 10 which incorporates the principles of the present invention. The filter probe 10 includes a housing 12, illustrated as partially broken away in FIG. 1, such housing serving to contain an inertial filter 14, a sample dilution block 16, an exhaust eductor 18 and various other components of the subject invention as will be hereinafter described. A supply interface 20 permits passage through the housing 12 by a compressed air line 22, a diluted sample line 24, a clean air line 26, and a filter pressure sensing/calibrator input line 28.

Lines 22, 24, 26 and 28 are bundled together and are protected by a sheathing 30. Compressed air line 22 is coupled by fitting 32 to the exhaust eductor 18 as shown only in FIG. 1. Diluted sample line 24 is coupled to the dilution block 16 by a fitting 34 and provides an output for the sample dilution block 16. Clean air line 26 is coupled by a fitting 36 to the sample dilution block 16 and pressure sensor/gas input line 28 is coupled by a fitting 38 to the inertial filter 14.

The inertial filter 14 includes an outer cylinder 40 and has disposed therein a filter 42 having a longitudinal bore 44. The filter 42 is sized so that a collection chamber 46 is formed between the filter 42 and the outer cylinder 40. Also disposed in the outer cylinder 40 is a heating unit 48 (shown only in FIG. 3) of a conventional thermostatically controlled design. The heating element 48 serves to heat the chamber 46 and therefore the filter 42. Similarly, the sheathing 30 is also preferably heated.

The longitudinal bore 44 of the filter 42 is in communication on the end 50 thereof with a probe 52 having a mounting flange 54. The probe 52 is coupled to the filter 42 by a fitting 56. The flange 54 is for mounting on the wall of a stack S, with the section 58 of the probe 52 extending into the stack gas.

The other end 60 of the filter 42 is coupled by a fitting 62 to the exhaust eductor 18. Axially mounted in the fitting 62 is a fitting 64 that couples bypass tube 66 on one end thereof to the bore of filter 42, the bypass tube 66 being in communication on the other end thereof with the chamber 46 of the inertial filter 14 as coupled through a coupling 68. The coupling 68 also is in communication with the sample dilution block 16. Sample dilution block 16 includes a filter 70 disposed adjacent to the coupling 68 and a filter 72 disposed adjacent to the fitting 36. Formed within the sample dilution block is a dilution chamber 74 which is in communication with the coupling 68 through the filter 70 and with the clean air line 26 through the coupling 36 and filter 72. Also in communication with the dilution chamber 74 is the diluted sample line 24.

The eductor 18 is provided with a eductor exhaust 76. The filter 42 can be constructed of a porous ceramic or porous metallic material as is well known in the art.

Although the operation of the subject invention is performed by the apparatus shown in FIGS. 1 and 2, the operation thereof can best be understood by viewing the pictorial representation of the subject invention shown in FIG. 3. Therefore, with reference to FIGS. 1, 2 and particularly FIG. 3, the probe 52 has the mounting flange 54 thereof mounted to a stack S such that the section 58 is exposed to a sample of stack gas G. The probe 52 has longitudinal bore 78 thereof in communication with the input of the inertial filter 14 through coupling 56. Disposed within the inertial filter 14 is the filter 42 having a longitudinal bore 44 in communication with the longitudinal bore 78 of the probe 52 on an end 50 thereof. The other end 60 of the filter 42 is in communication with the fitting 62 and the central bore of the exhaust eductor 18.

The exhaust eductor 18 is fed compressed air through compressed air line 22. As a result of the introduction of compressed air into the eductor through the port 80 thereof, a suction effect is created and gas G is extracted from the stack sand is drawn through the probe 52 and the filter 42 out through the eductor 18 and through the exhaust 82 thereof.

The compressed air at air line 22 is regulated so that the stack gas is drawn through the filter element at a high speed such that particles moving at high speed along the axis of the tubular filter 42 have too much inertia to stick to the filter walls, while gaseous constituents permeate through the porous filter body at right angles to the direction of flow. Of course, this is expedited by the heating of the ceramic filter element 42 by the heater 48.

The constituents which permeate the filter 42 are temporarily collected in the collection chamber 46 of the inertial filter 14. The chamber 46 is in communication with the dilution block 16 through the coupling 68. The material collected in the chamber 46 is drawn into the dilution chamber 74 of the dilution block 16 through filter 70 and a critical flow orifice 84. Simultaneously, air from a clean source is supplied through clean air line 26 and through filter 72 to a second critical flow office 86 and ultimately is supplied so it mixes within dilution chamber 74 with the gas constituent entering through critical orifice 84.

In the preferred embodiment of the present invention the filters 70 and 72 are constructed of porous metal frit which permits passage of materials up to 2 microns and the critical flow orifice has a diameter of 4 mils. This sets up a ratio with a range of 15 to 1 and 300 to 1 which can be selected by varying the size of the critical flow orifices used in conjunction with selected analyzers. The gas constituent which is diluted by the air in dilution chamber 74 is drawn therefrom by a sample pump 88, shown in FIG. 3, the output 90 thereof which is fed to suitable analyzing instruments, well known in the art.

Crucial to the subject invention is the bypass tube or loop 66 which is in communication on one end thereof through fitting 68 with the gaseous constituent input of the sample dilution block 16 and on the other end thereof through fitting 64 to the output of the longitudinal bore of the filter 44. A bypass flow restrictor 92 of the valve type may be disposed in the bypass line 66 as shown in FIG. 3. The effect of the bypass tube 66 is to create a bypass loop so that there is a continuous flow of gas constituent from the chamber 46 past the filter 70 of the sample dilution block 16. As a result, rather than the sample block 16 providing a reading which is the average of collected constituent, what essentially is provided is an instantaneous or real time measurement of the flow of the gas from the stack S into the probe 52.

Also shown in FIG. 3 is a filter pressure sensing and gas inlet line 28 connected to a selection valve 94. Selection valve 94 can alternatively couple pressure sensor 96 or calibration gas line 98 to which calibration gas is supplied to the chamber 46 of the inertial filter 14. This permits adjustment of the pressure within the chamber 46 with a correction factor so any pressure related errors in the dilution ratio can be corrected.

It therefore should be clear that the present invention provides a filter probe for sampling components of a stack gas which, through use of an inertial bypass filter, provides a filter surface that is without danger of clogging because of gas moving at a high speed in an inline flow through a heated ceramic or metallic filter element. As such, particles moving at a high speed along the axis of the tubular filter have too much inertia to stick to the filter walls. Nonetheless, gaseous constituents permeate through the porous filter body and then these hot gas samples are drawn off into a dilution mixer where the hot moisture laden sample is diluted with clean air in a ratio predetermined by the parameters of the mixer such as the critical flow orifices and the design of the sample pump 88 to obtain a sample which is lower in temperature and lower in relative humidity than the stack gases directly extracted by the probe. This conditioned sample is therefore directly usable in gas analyzers without concern over condensation.

As a result of such configuration, a very rugged and trouble free sample conditioning system is provided that permits wet basis of sample analysis when this mode of measurement is preferred by the user. Further, incorporated into the configuration is dilution ratio stability with temperature and stack pressure. Control of dilution mixer temperature with thermostatically operated heater elements well known in the art eliminates the effects of temperature on the ratio of flow through the two critical flow orifices and the availability of a tube connection to the space around the inertial filter affords the ability to sense the pressure at that point and to apply correction factors to any pressure related errors of the dilution ratio to the computer which controls the data read from the analyzers. Of course, the analyzers are well known in the art and will not be herein discussed.

It will be understood that various changes in the details, materials, arrangements of parts and operational conditions which have been herein described and illustrated in order to explain the nature of the invention may be made by those skilled in the art within the principles and scope of the invention.

Having thus set forth the nature of the invention, what is claimed is:

1. A filter probe for sampling components of a stack gas comprising:
   means for extracting a flowing sample of said stack gas, said extracting means having a flow input and a flow output, said flowing sample flowing from said flow input to said flow output;
   means for filtering said flowing stack gas sample extracted by said extracting means, said filtering means being in communication with said flowing sample in said extracting means;
   means for collecting said flowing stack gas sample after filtering by said filtering means, said collecting means being in communication with said flowing stack gas sample after filtering by said filtering means;
   means for conditioning said filtered and said collected stack gas sample based on predetermined criteria, said conditioning means being in communication with said collecting means; and
   bypass means for flowing a portion of the filtered and collected stack gas sample from said collecting means to said flow output of said extracting means bypassing said conditioning means so as to permit a constant flow of said filtered stack gas sample to said conditioning means, said bypass means being in communication with said collecting means and said flow output of said extracting means.

2. A filter probe in accordance with claim 1, wherein said extracting means comprises a probe element disposed in a stack through which a stack gas flows, said probe element serving as the flow input of said extracting means.

3. A filter probe in accordance with claim 2, wherein said extracting means further comprises eductor means, said eductor means being disposed proximate to and in communication with the flow output of said extracting means, said eductor means for regulating the flow of said stack gas through said extracting means.

4. A filter probe in accordance with claim 1, wherein said extracting means further comprises eductor means, said eductor means being disposed proximate to the flow output of said extracting means, said eductor means for regulating the flow of said stack gas through said extracting means.

5. A filter probe in accordance with claim 2, wherein said filtering means has disposed therethrough a chamber for accommodating the flow therethrough of the flowing sample of stack gas.

6. A filter probe in accordance with claim 1, wherein said filtering means has disposed therethrough a chamber for accommodating the flow therethrough of the flowing sample of stack gas.

7. A filter probe in accordance with claim 5, wherein said filtering means comprises a filter medium, said chamber being elongated and having two ends, said chamber being disposed in said filter medium, one end of said chamber being in communication with said probe element.

8. A filter probe in accordance with claim 7, wherein said filter medium is cylindrical, said chamber being disposed longitudinally therein.

9. A filter probe in accordance with claim 3, wherein said eductor means comprises an air driven eductor, said air driven eductor for providing suction.

10. A filter probe in accordance with claim 3, wherein said filtering means comprises a chamber for accommodating the flow therethrough of the flowing sample of stack gas, said chamber being in communication on one end thereof with said probe element and on the other end thereof with said eductor means.

11. A filter probe in accordance with claim 10, wherein said filter means comprises a filter medium, said chamber being elongated and having two ends, said chamber being disposed in said filter medium, one end of said chamber being in communication with said probe element, the other end of said chamber being in communication with said eductor means.

12. A filter probe in accordance with claim 11, wherein said filter medium is cylindrical, said chamber being disposed longitudinally therein.

13. A filter probe in accordance with claim 6, wherein said filter means comprises a filter medium, said chamber being elongated and having two ends, said chamber being disposed in said filter medium, the flow of the flowing sample of stack gas being from one end of the chamber to the other end of the chamber.

14. A filter probe in accordance with claim 13, wherein said collecting means comprises an envelope enclosing said filter medium, said envelope for collecting the flowing stack gas sample after the flowing stack gas sample is filtered by said filter medium.

15. A filter probe in accordance with claim 14, wherein said filter medium is cylindrical and said envelope is cylindrical, said envelope being coaxially disposed about said filter medium, a collection chamber being formed by the space between said filter medium and said envelope.

16. A filter probe in accordance with claim 14, wherein said envelope is heated.

17. A filter probe in accordance with claim 1, wherein said collecting means is heated.

18. A filter probe in accordance with claim 14, further comprising means for providing a calibration gas to said envelope.

19. A filter probe in accordance with claim 1, wherein said conditioning means comprises a first secondary filter in communication on one side thereof with said collecting means, a second secondary filter in communication on one side thereof with a clean source of air, a first critical flow orifice in communication on one side thereof with the other side of said first secondary filter, a second critical flow orifice in communication on one side thereof with the other side of said second secondary filter, said conditioning means further comprising a suction pump having an input and an output, the input of said suction pump being in communication with the other sides of said first and second critical flow orifices, the output of said suction pump being adapted to be in communication with predetermined analysis means.

20. A filter probe in accordance with claim 19, further comprising a housing, said first and second secondary filters and said first and second critical flow orifices being disposed therein.

21. A filter probe in accordance with claim 20, further comprising means for maintaining said housing at a preselected temperature.

22. A filter probe in accordance with claim 1, wherein said bypass means comprises a valve in communication on one side thereof with said collecting means, the other side of said valve being in communication with said flow output of said extracting means.

23. A filter probe in accordance with claim 9, wherein said bypass means comprises a valve in communication on one side thereof with said collecting means, the other side of said valve being in communication with said flow output of said extracting means.

24. A filter probe in accordance with claim 8, wherein said flowing means comprises a valve in communication on one side thereof with said collecting means, the other side of said valve being in communication with said flow output of said extracting means.

* * * * *